United States Patent [19]
Marhold

[11] Patent Number: 6,077,973
[45] Date of Patent: Jun. 20, 2000

[54] PROCESS FOR THE PREPARATION OF ANILINES WHICH CONTAIN FLUORINE AND NEW ANILINES WHICH CONTAIN FLUORINE

[75] Inventor: Albrecht Marhold, Leverkusen, Germany

[73] Assignee: Bayer Aktiengesellschaft, Leverkusen, Germany

[21] Appl. No.: 07/984,079

[22] Filed: Nov. 30, 1992

[30] Foreign Application Priority Data

Dec. 9, 1991 [DE] Germany ............... 41 40 536

[51] Int. Cl.$^7$ ............................................. C07C 209/00
[52] U.S. Cl. .......................................................... 564/406
[58] Field of Search ............................................. 564/406

[56] References Cited

U.S. PATENT DOCUMENTS 4,521,622  6/1985  Andoh et al. ........................... 564/406

FOREIGN PATENT DOCUMENTS 2008557  7/1990  Canada .
0140783  10/1984  European Pat. Off. .
0315862  5/1989  European Pat. Off. .
0381010  8/1990  European Pat. Off. .

OTHER PUBLICATIONS

William A. Sheppard, *The Journal of Organic Chemistry*, 1964, pp. 1–11, Month Unavailable.

Bernard Langlois, *Bull. Soc. Chim. France*, 1986, pp. 925–929, Month Unavailable.

The Journal of Organic Chemistry, vol. 29, No. 1; Jan. 13, 1964; pp. 1–11, William A. Sheppard, "Fluorinated Ethers" "Aryl Fluoroalkyl Ethers".

*Primary Examiner*—Samuel Barts
*Attorney, Agent, or Firm*—Norris, McLaughlin & Marcus, P.A.

[57] ABSTRACT

Anilines which contain fluorine in a side chain are prepared by reacting chlorinated aromatic compounds with ammonia in the presence of a catalyst and optionally water at 200 to 280° C. Some of the trifluoromethoxyanilines which may be prepared in this way are new compounds.

6 Claims, No Drawings

PROCESS FOR THE PREPARATION OF ANILINES WHICH CONTAIN FLUORINE AND NEW ANILINES WHICH CONTAIN FLUORINE

The present invention relates to a process for the preparation of anilines which contain fluorine in a side chain from the corresponding chlorinated aromatic compounds, and to new anilines which contain fluorine in a side chain.

It is known that 2-trifluoromethoxy-chlorobenzene may be reacted with sodium amide to give 3-trifluoromethoxyaniline (see EP-A2 0 140 783). The disadvantages here are the use of expensive sodium amide, which is difficult to handle, and the impossibility of preparing 2- and 4-trifluoromethoxy-anilines by this process.

Furthermore, it is known that trifluoromethoxyanilines may be obtained by nitrating and reducing trifluoromethoxybenzene (see Bull. Soc. Chim. France 1986, no. 6, p. 925). The disadvantage here is that the trifluoromethoxyanilines are always produced in the form of a mixture of the ortho and para isomers because selective introduction of the nitro group is not possible. Metatrifluoromethoxy-anilines are not accessible at all in this way.

Finally, it is known that 3-nitrophenylfluoroformate may be reacted with sulphur tetrafluoride, and the 3-nitro-trifluoromethoxybenzene obtainable in this way may be reduced to give 3-trifluoromethoxyaniline (see J. Org. Chem. 29 (1), p. 1–11 (1964)). The use of very toxic and expensive sulphur tetrafluoride, however, is very disadvantageous because it requires special measures, as well as the disposal of the thionyl fluoride which is produced.

A process has now been found for the preparation of anilines which contain fluorine in a side chain, of the formula (I)

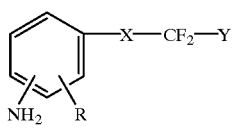

(I)

in which
R represents hydrogen, chlorine, $C_1$–$C_4$-alkyl or $C_1$–$C_4$-alkoxy,
X represents oxygen or sulphur and
Y represents fluorine, $CF_3$ or $CF_2Cl$ or, together with the $CF_2$—X radical, represents an —O—$CF_2$—$CF_2$—O group whose two oxygen atoms are bonded in the o-position to each other in the aromatic ring,
characterised in that chlorinated aromatic compounds of the formula (II)

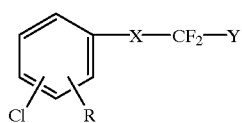

(II)

in which
R, X and Y have the meaning given for formula (I),
are reacted with ammonia in the presence of a catalyst and optionally water at 200 to 280° C.

Chlorinated aromatic compounds of the formula (II) which are suitable for the process according to the invention are commercial products or can be prepared by known processes (see e.g. Houben-Weyl, Methoden der organischen Chemie [Methods in Organic Chemistry], vol. E4, p. 626–644 (1983)).

Chlorinated aromatic compounds of the formula (II) for use in the process according to the invention are preferably those in which
R represents hydrogen, chlorine, methyl, ethyl, methoxy or ethoxy,
X represents oxygen and
Y represents fluorine.

Catalysts which are suitable for the process according to the invention are, for example, compounds of iron, cobalt, nickel, zinc and silver mixed with copper or copper compounds. Halides of nickel and copper, optionally mixed with copper, are preferred. Copper oxide and copper halides are particularly preferred. The catalyst may be used in the process according to the invention in an amount of for example 0.1 to 20% by weight, relative to the chlorinated aromatic compound of the formula (II) which is used. Preferably, this amount is 1 to 15% by weight.

The process according to the invention may be performed in the presence or absence of water. Preferably, it is performed in the presence of water. For example, water may be used in the process according to the invention in an amount of 20 to 500% by weight, relative to the chlorinated aromatic compound of the formula (II) which is used. Preferably, this amount is 50 to 200% by weight.

The ammonia required for the process according to the invention is preferably added as a liquid. 40 to 500 ml of liquid ammonia may be used, for example, per 100 g of chlorinated aromatic compound of the formula (II) which is used. Preferably, this amount is 50 to 250 ml.

The process according to the invention is performed at temperatures in the range 200 to 280° C. Temperatures in the range 220 to 260° C. are preferred.

In general, the reaction according to the invention is complete after 5 to 20 hours.

In a preferred industrial embodiment of the process according to the invention the procedure is as follows: the chlorinated aromatic compound of the formula (II), water and the catalyst are initially introduced into an autoclave and liquid ammonia is metered in afterwards. The mixture is then heated to the desired reaction temperature for 5 to 20 hours, with stirring. The autoclave is then cooled to room temperature, the pressure is released and excess ammonia is recovered. Finally, the organic phase is steam-distilled or extracted and optionally distilled.

The process according to the invention has a number of advantages. It allows the preparation of anilines of the formula (I) which contain fluorine in a side chain with generally good conversions and satisfactory yields. It is essential to the process according to the invention that the amino group enters selectively wherever a chlorine atom was bonded previously. In addition, the use of dichloroaromatic compounds of the formula (II) permits selective preparation of the monochloroanilines of the formula (I). Surprisingly, isomeric mixtures do not occur and the Y—$CF_2$—X group, which is called a superhalide in J. Am. Chem. Soc. 85 (2), p. 1314–1318 (1963), is not exchanged for an amino group. Thus it could not be expected that the process according to the invention would yield such good results.

The process according to the invention is very particularly suitable for the preparation of anilines of the formula (I) which contain fluorine in a side chain in which
R represents hydrogen, chlorine, methyl, ethyl, methoxy or ethoxy,
X represents oxygen and
Y represents fluorine or $CF_3$.

Furthermore, the present invention relates to trifluoromethoxyanilines of the formula (III)

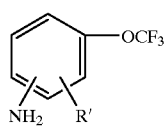

(III)

in which the NH$_2$ group is located in the o- or m-position to the CF$_3$—O group and in which R' represents chlorine in the o- or m-position to the CF$_3$—O group or methyl in the p-position to the CF$_3$—O group.

Preferred trifluoromethoxyanilines of the formula (III) are 3-trifluoromethoxy-5-chloro-aniline, 2-chloro-3-trifluoromethoxy-aniline, 2-trifluoromethoxy-5-methyl-aniline and 2-trifluoromethoxy-3-chloro-aniline.

The preparation of the trifluoromethoxyanilines of the formula (III) is described above. Trifluoromethoxyanilines of the formula (III) may be used as intermediates for dyes, crop protection agents and drugs.

EXAMPLES

General:

In each case, the stated amounts of a chlorinated aromatic compound of the formula (II), water and catalyst were initially placed in an autoclave and the amount of liquid ammonia given in each case was added under pressure. In each case, the mixture was heated at the given temperature for the given time with stirring. The autoclave was then cooled to room temperature, the pressure was released, the organic phase was separated from the aqueous phase and the organic phase was steam-distilled. The organic phase was separated from the distillate, weighed and analysed. The individual examples performed are summarised in detail in the following Table.

Physical data for some of the compounds of the formula (I) which were prepared.

3-chloro-5-amino-trifluoromethoxybenzene (Example 8):
  Boiling point: 94 to 95° C. at 12 mbar
  Refractive index: $n_D^{20}$: 1.4940
2-chloro-3-amino-trifluoromethoxybenzene (Example 9):
  Boiling point: 102 to 103° C. at 14 mbar
  Refractive index: $n_D^{20}$: 1.4982
2-amino-4-methyl-trifluoromethoxybenzene (Example 10):
  Boiling point: 40 to 41° C. at 10 mbar
  Refractive index: $n_D^{20}$: 1.4435
2-amino-6-chloro-trifluoromethoxybenzene (Example 15):
  Boiling point: 92 to 94° C. at 15 mbar
  Refractive index: $n_D^{20}$: 1.5020

What is claimed is:

1. A process for the preparation of anilines of the formula (I) which contain fluorine in a side chain,

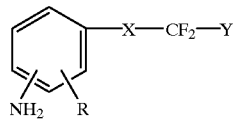

(I)

in which
  R represents hydrogen, chlorine, C$_1$–C$_4$-alkyl or C$_1$–C$_4$-alkoxy,
  X represents oxygen or sulphur and
  Y represents fluorine, CF$_3$ or CF$_2$Cl or, together with the CF$_2$—X radical, represents an —O—CF$_2$—CF$_2$—O— group whose two oxygen atoms are bonded in o-position to each other in the aromatic ring, in which a chlorinated aromatic compound of the formula (II)

TABLE

| Example No. | Chlorinated aromatic compound of the formula (II)* | | | | Amount (g) | Amount of water (ml) | Amount of ammonia (ml) | Catalyst and amount | | Temperature (° C.) | Reaction time (h) | Aniline of the formula (I)* obtained | | | | Conversion (%) | Yield (%) |
|---|---|---|---|---|---|---|---|---|---|---|---|---|---|---|---|---|---|
| | R | Cl | X | Y | | | | | | | | R | NH$_2$ | X | Y | | |
| 1 | H | 4 | O | F | 100 | 100 | 150 | CuCl | 10 | 250 | 6 | H | 4 | O | F | 86 | 78.8 |
| 2 | H | 4 | O | F | 50 | 50 | 50 | CuCl | 1 | 230 | 10 | H | 4 | O | F | 85 | 14.2 |
| 3 | H | 2 | O | F | 100 | 100 | 130 | CuCl | 15 | 250 | 15 | H | 2 | O | F | 93.8 | 72.3 |
| 4 | H | 2 | O | F | 100 | 100 | 150 | CuCl | 10 | 250 | 6 | H | 2 | O | F | 70 | 53.5 |
| 5 | H | 2 | O | F | 50 | 50 | 70 | CuBr | 5 | 240 | 10 | H | 2 | O | F | 71 | 28.8 |
| 6 | H | 3 | O | F | 100 | 100 | 130 | CuCl | 10 | 250 | 10 | H | 3 | O | F | 82 | 63 |
| 7 | H | 4 | S | F | 50 | 50 | 70 | CuCl | 3 | 250 | 7 | H | 4 | S | F | 90 | 88 |
| 8 | 3-Cl | 5 | O | F | 50 | 50 | 50 | CuCl | 5 | 240 | 10 | 3-Cl | 5 | O | F | 93 | 59 |
| 9 | 2-Cl | 3 | O | F | 100 | 100 | 120 | CuCl | 10 | 250 | 8 | 2-Cl | 3 | O | F | 52 | 18 |
| 10 | 4-CH$_3$ | 2 | O | F | 100 | 100 | 130 | CuCl | 10 | 250 | 15 | 4-CH$_3$ | 2 | O | F | 89 | 56 |
| 11 | 4-Cl | 3 | O | F | 50 | 50 | 60 | Cu/CuCl | 10 | 250 | 10 | 4-Cl | 3 | O | F | 92 | 54 |
| 12 | 2-Cl | 5 | O | F | 40 | 50 | 50 | CuCl | 5 | 250 | 10 | 2-Cl | 5 | O | F | 75.8 | 62 |
| 13 | H | 3-Cl | —O(CF$_2$)$_2$O— 5,6 | | 14 | 30 | 30 | CuCl | 1 | 250 | 8 | H | 3 | —O(CF$_2$)$_2$O— 5,6 | | 100 | 51 |
| 14 | 2-Cl | 4 | O | F | 200 | 200 | 200 | CuCl | 15 | 230 | 7 | 2-Cl | 4 | O | F | 53 | 87.5 |
| 15 | 6-Cl | 2 | O | F | 100 | 100 | 100 | CuCl | 10 | 240 | 10 | 6-Cl | 2 | O | F | 77 | 72.4 |
| 16 | H | 4 | O | CF$_3$ | 100 | 100 | 120 | CuCl | 15 | 250 | 10 | H | 2 | O | F | 84 | 77.5 |

*)Numbers refer to the position relative to the Y-CF$_2$-X group,
O repreeents oxygen,
S represents sulphur,
F represents fluorine.

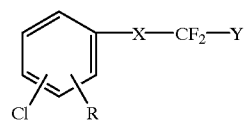

in which

R, X and Y have the meaning given for the formula (I), is reacted with ammonia in the presence of a catalyst at 200 to 280° C.

2. The process of claim 1, in which water is present.

3. The process of claim 1, in which the catalyst used is a compound of iron, cobalt, nickel, zinc or silver mixed with copper or a copper compound.

4. The process of claim 1, in which copper oxide or a copper halide is used as the catalyst.

5. The process of claim 1, which is performed in the presence of 20 to 500% by weight of water, relative to the chlorinated aromatic compound of the formula (II) which is used.

6. The process of claim 1, in which 40 to 500 ml of liquid ammonia are used per 100 g of the chlorinated aromatic compound of the formula (II) which is used.

* * * * *